(12) United States Patent
Hamilton

(10) Patent No.: US 10,295,459 B1
(45) Date of Patent: May 21, 2019

(54) OBJECT ILLUMINATION SYSTEMS

(71) Applicant: Dax Hamilton, Aumsville, OR (US)

(72) Inventor: Dax Hamilton, Aumsville, OR (US)

( * ) Notice: Subject to any disclaimer, the term of this patent is extended or adjusted under 35 U.S.C. 154(b) by 0 days.

(21) Appl. No.: 15/837,923

(22) Filed: Dec. 11, 2017

(51) Int. Cl.
*G01J 3/46* (2006.01)
*G01N 21/27* (2006.01)
*F21V 8/00* (2006.01)
*G01N 21/88* (2006.01)

(52) U.S. Cl.
CPC ......... *G01N 21/27* (2013.01); *G01N 21/8806* (2013.01); *G02B 6/0055* (2013.01); *G02B 6/0068* (2013.01); *G02B 6/0091* (2013.01); *G01N 2201/08* (2013.01)

(58) Field of Classification Search
CPC combination set(s) only.
See application file for complete search history.

(56) References Cited

U.S. PATENT DOCUMENTS

2007/0177138 A1\* 8/2007 Esmaeili ............ G01N 21/8806
356/241.1

\* cited by examiner

*Primary Examiner* — Abdullahi Nur
(74) *Attorney, Agent, or Firm* — Mohr Intellectual Property Law Solutions, PC

(57) ABSTRACT

Systems and apparatuses of operating the same are described. An apparatus that may include a light guide. The light guide may include a body configured to direct at least a portion of light within a defined wavelength spectrum from a first light source toward an object. The body may be formed of a material to provide a threshold contrast ratio between a first portion of the object and a second portion of the object. The body may include a first surface that includes a first cavity formed to receive at least a portion of an incident end the first light source. The body may include a second surface at a distal end from the light source. The second surface may be a peripheral diffusing portion or a peripheral focusing portion.

20 Claims, 10 Drawing Sheets

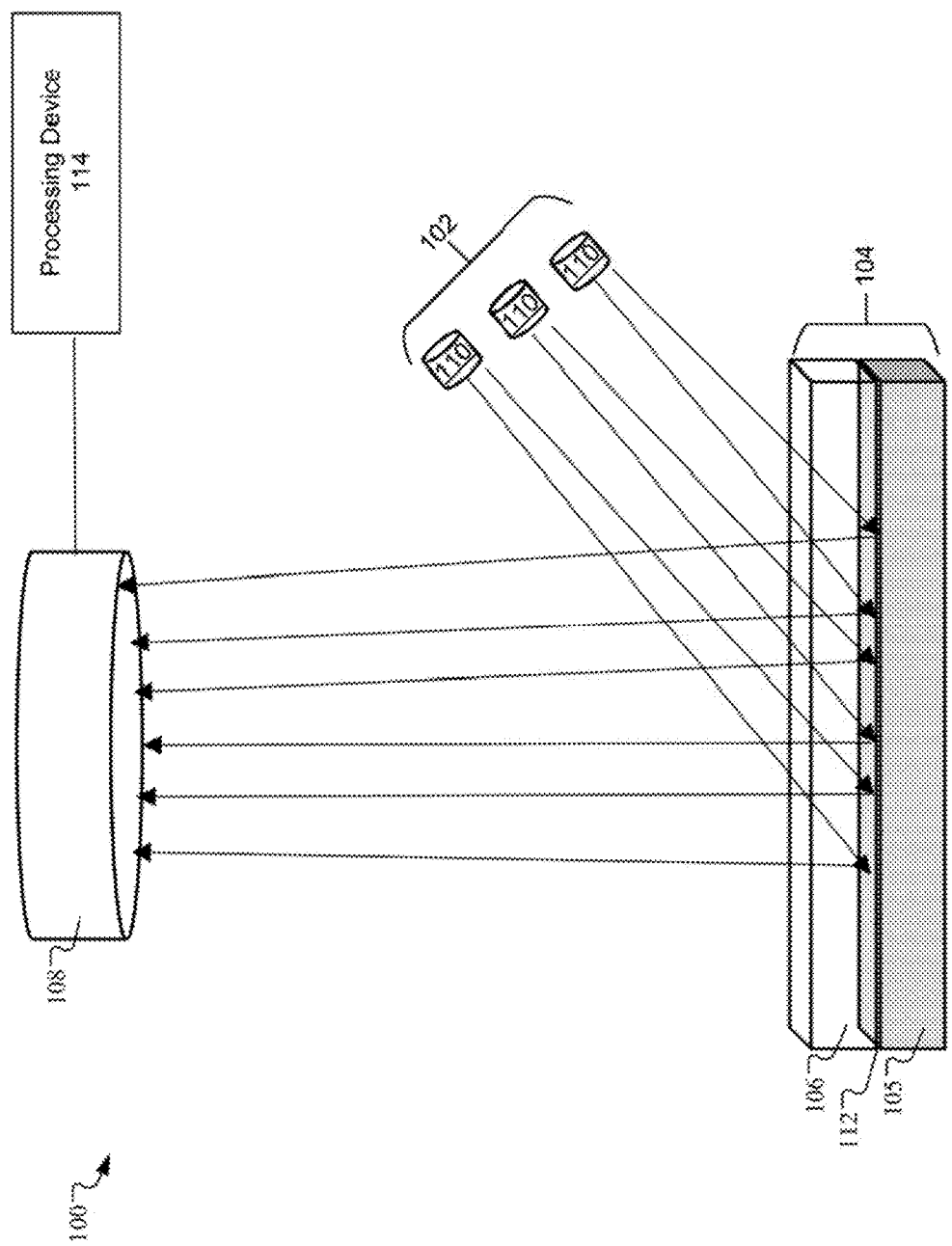

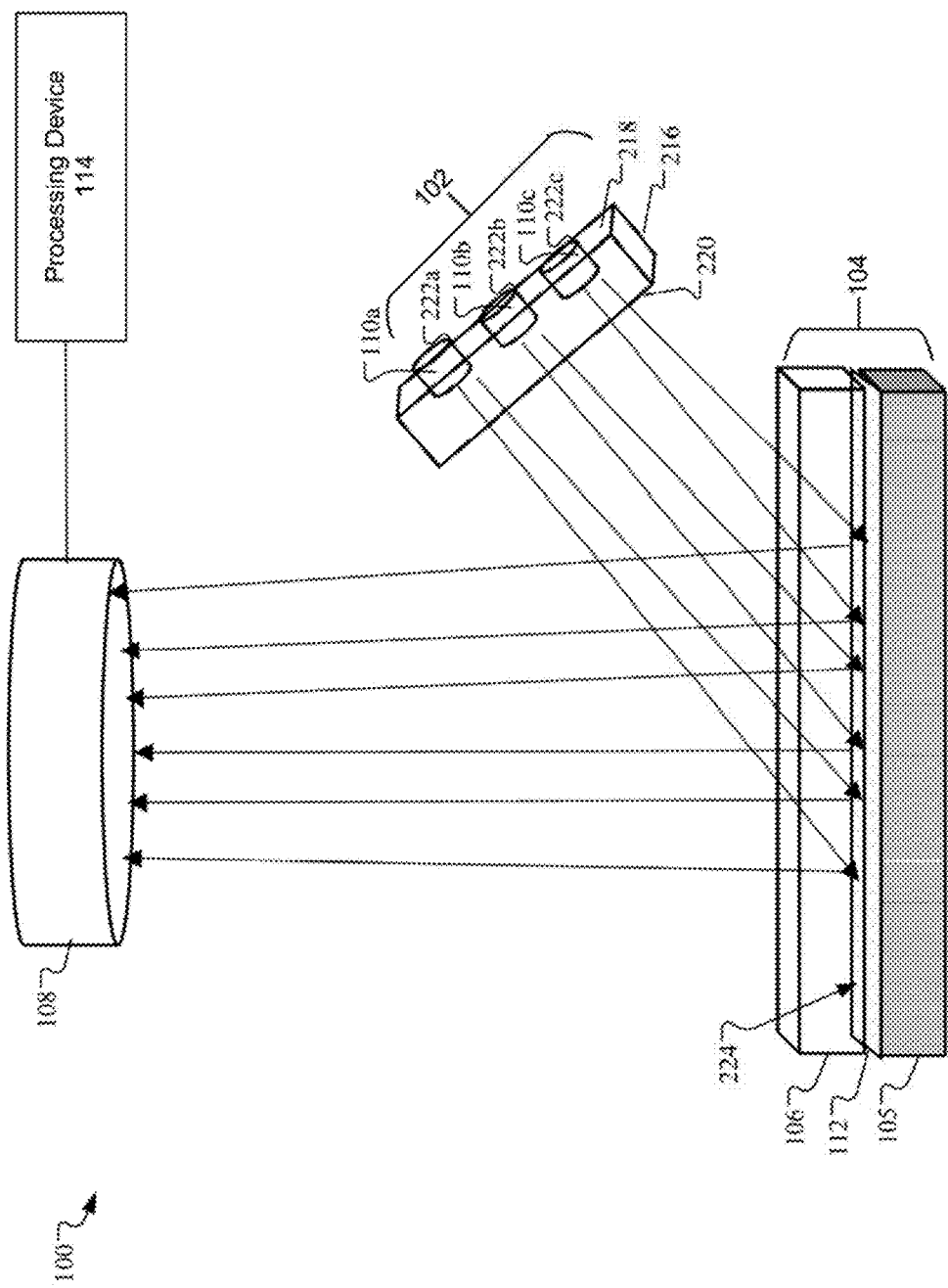

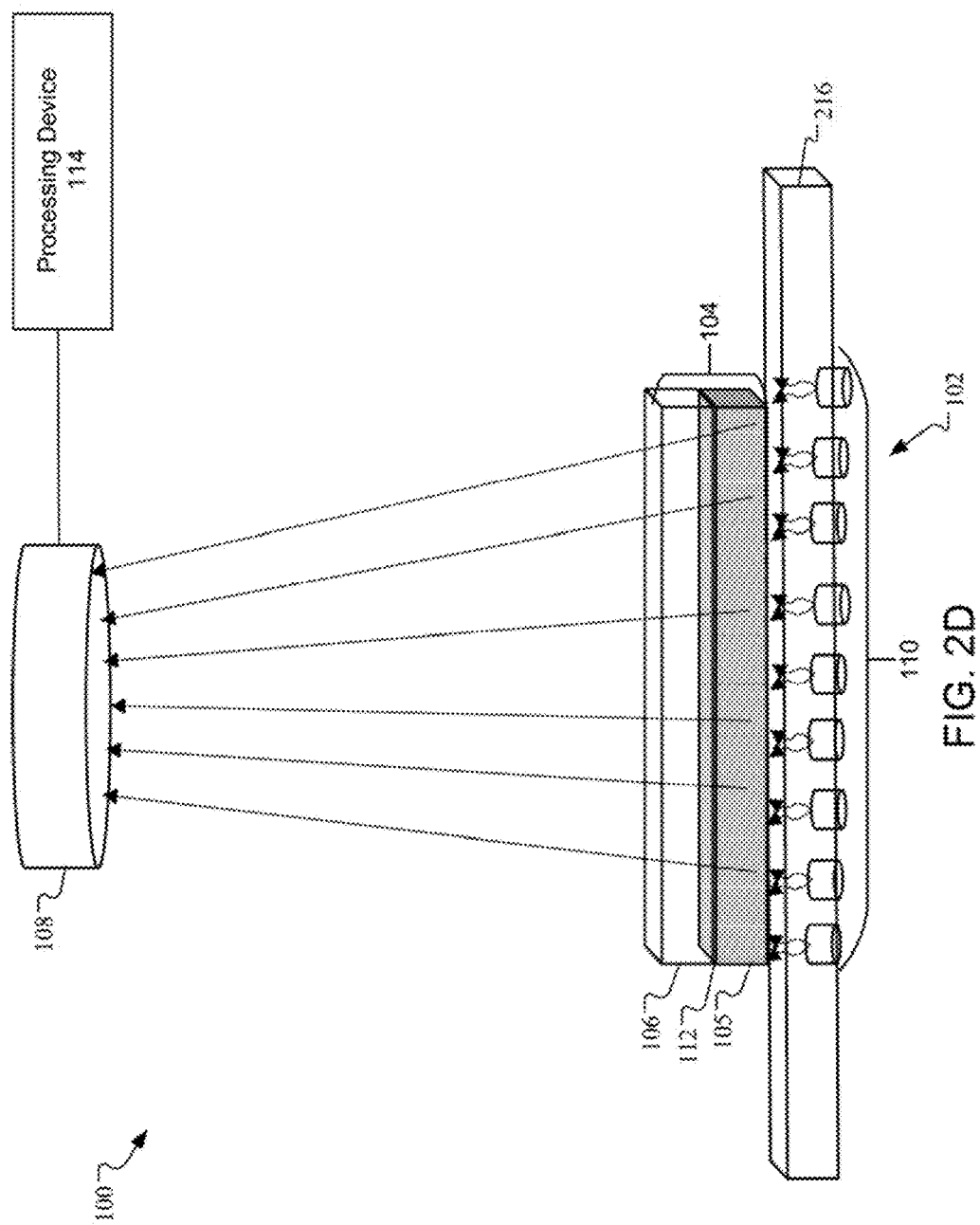

OBJECT ILLUMINATION SYSTEMS

BACKGROUND

Objects undergo an inspection process prior to being used in order to ensure quality, aesthetics, and reduce a risk of failure. Objects of an aesthetic nature may be inspected for imperfections. Objects that are critical to an operation of a machine may be inspected for imperfections and defects to reduce or eliminate failure of the objects during the operation of the machine.

SUMMARY

An apparatus that may include a light guide. The light guide may include a body configured to direct at least a portion of light within a defined wavelength spectrum from a first light source toward an object. The body may be formed of a material to provide a threshold contrast ratio between a first portion of the object and a second portion of the object. The body may include a first surface that includes a cavity formed to receive at least a portion of an incident end the light source. The body may include a second surface at a distal end from the light source. The second surface may be a peripheral diffusing portion or a peripheral focusing portion.

BRIEF DESCRIPTION OF THE DRAWINGS

The present description will be understood more fully from the detailed description given below and from the accompanying drawings of various embodiments of the present embodiment, which, however, should not be taken to limit the present embodiment to the specific embodiments, but are for explanation and understanding only.

FIG. 1 shows an object illumination system, according to an embodiment.

FIG. 2B shows the object illumination system in FIG. 1 with an absorber, according to an embodiment.

FIG. 2D shows the object illumination system in FIG. 1 with the light source and the light guide located below the object, according to an embodiment.

DETAILED DESCRIPTION

Figure 2A:
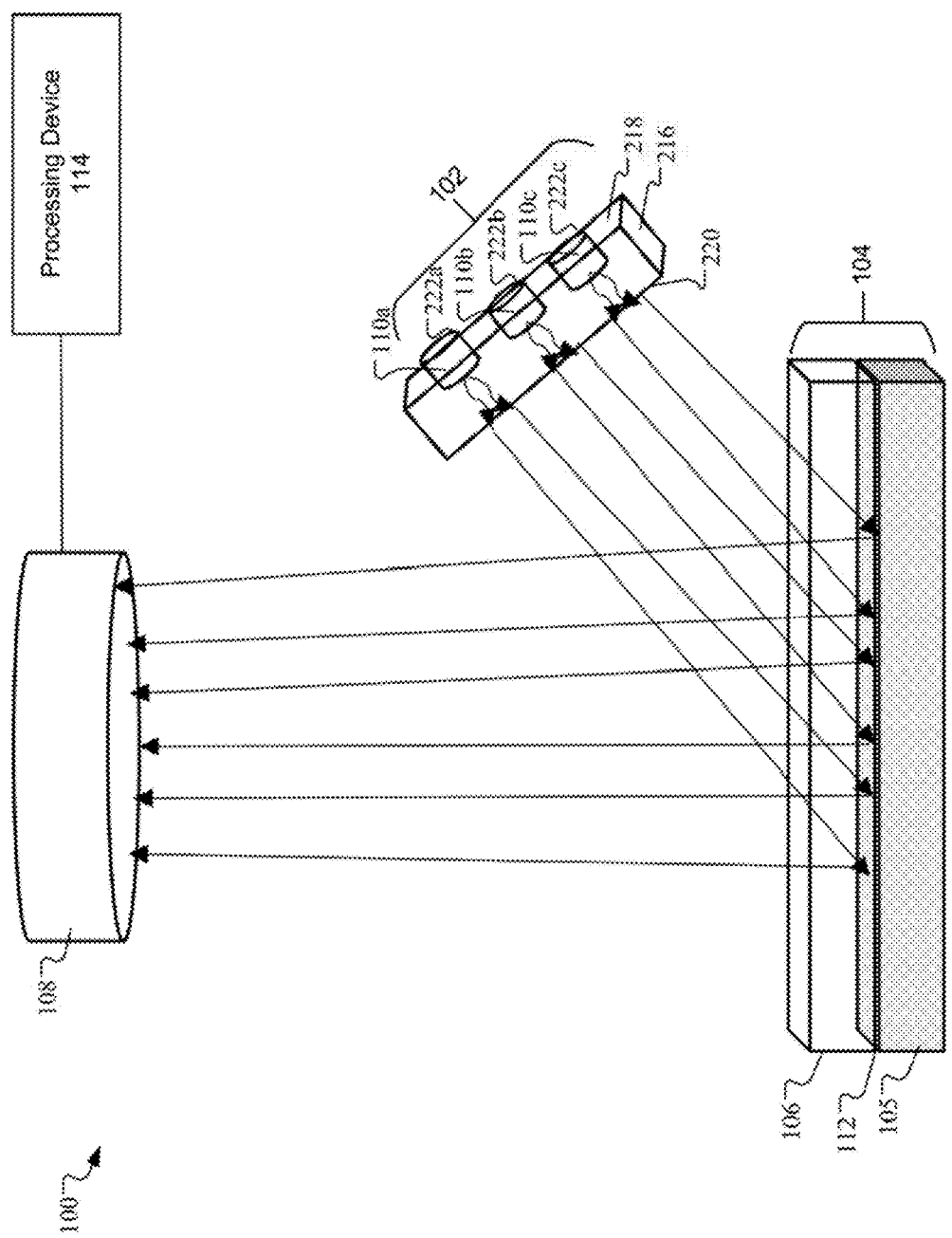
FIG. 2A shows the object illumination system in FIG. 1 with a light guide, according to an embodiment.

The disclosed object illumination systems will become better understood through a review of the following detailed description in conjunction with the figures. The detailed description and figures provide merely examples of the various embodiments described herein. Those skilled in the an will understand that the disclosed examples may be varied, modified, and altered without departing from the scope of the embodiments described herein. Many variations are contemplated for different applications and design considerations; however, for the sake of brevity, each and every contemplated variation is not individually described in the following detailed description.

Throughout the following detailed description, examples of various object illumination systems are provided. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

Objects used for various applications may undergo an inspection process prior to being used. For example, objects of an aesthetic nature may be inspected for imperfections to ensure quality control of the objects. Objects that are critical to an operation of a machine may be inspected for imperfections and defects to reduce or eliminate failure of the objects during the operation of the machine. Objects that are joined together by welding or bonding may be inspected to verify the integrity of the weld and the objects after the welding or bonding process.

There are various processes to inspect the objects. In one example, an individual may visually inspect the object to identify surface imperfections in the object. In another example, an optical system may employ an light sensor to capture image data of the object and inspect the object using a software analysis program. An accuracy of the inspection of the object may vary based on environmental conditions. For example, the lighting conditions of the environment where the object is inspected may cause the accuracy of the inspection of the object to vary. When the lighting level is low, imperfections in the object may not be visible. When the light level is bright, imperfections in the object maybe washed out by the light, The radiation pattern of the light may also vary the inspection accuracy of the object. For example, when the light unevenly illuminates surfaces of the object, such as concave or convex surfaces, the imperfections of the object may not be visible or identified. Additionally, as the size and shape of the object varies, the accuracy of the inspection of the object may also vary. The variability of the accuracy of the inspection of the objects may lead to increased imperfections and failures of objects that were approved during inspections.

The embodiments described herein may address the above-noted deficiencies by providing an object illumination system to increase the accuracy of the inspections. The object illumination system may include a light guide to direct light from a light source and illuminate an object with light at a desired level. In one example, the light guide may diffuse or disperse light from a light source to evenly illuminate the object or a portion of the object. In another example, the light guide may focus the light from the light source to illuminate a portion of the object. The light guide may increase the accuracy of the object inspection by reducing or eliminating variations in the environment and/or variations in the inspection caused by varying sizes or shapes of the objects.

FIG. 1 shows an object illumination system 100, according to an embodiment. The object illumination system 100 may include a light source 102, an object 104, and an light sensor 108. The light source 102 may include one or more lighting elements 110. In one example, the lighting elements 110 may be incandescent light bulbs, halogen light bulbs, or fluorescent light bulbs. In another embodiment, the lighting elements 110 may be light emitting diodes (LEDs). The lighting elements 110 may radiate light at a defined wavelength or wavelength spectrum. In one embodiment, the light may be a low band ultraviolet light or a high band ultraviolet light with a wavelength spectrum ranging between 350 nanometers (nm) and 450 nm. In another embodiment, the light may be near-infrared light with a wavelength spectrum ranging between 750 nm and 1100 nm. In another embodiment, the light may be infrared light with a wavelength spectrum ranging between 1700 nm and 2000 nm. In another embodiment, the light may be a single wavelength of light, such as 1550 nm that is the wavelength of light absorbed by water The light may emit light towards the object 104. The object 104 may include a first portion 105 and a second portion 106. In one example, the first portion 105 and/or the second portion 106 may reflect at least a portion of the light. In another example, the first portion 105 and/or the second portion 106 may absorb at least a portion of the light.

In one embodiment, the first portion 105 and/or the second portion 106 may be transmissive material. In another embodiment, the first portion 105 and/or the second portion 106 may be absorptive material. In one example, the first portion 105 may be transmissive material and the second portion 106 may be transmissive material. In another example, the first portion 105 may include transmissive material and the second portion 106 may be absorptive material. In another example, the first portion 105 may include absorptive material and the second portion 106 may be transmissive material. In another example, the first portion 105 may include absorptive material and the second portion 106 may be absorptive material.

In one embodiment, the first portion 105 may be joined to the second portion 106. For example, the first portion 105 may be joined to the second portion 106 by laser welding, ultrasonic welding, gluing, solvent bonding, hot plate welding, infrared welding, and so forth. For example, laser welding may use a laser beam to provide a concentrated heat source to form narrow, deep welds and high welding rates between the first portion 105 and the second portion 106. The laser welding may be used in high volume applications using automation, such as in the automotive industry.

The joining technique may form a joint 112 where the first portion 105 and the second portion 106 are joined together. In one example, the light source 102 may illuminate the joint 112 for inspection. In another example, the illumination source 102 may illuminate at least a portion of the first portion 105 and/or the second portion 106 for inspection.

For example, the joint 112 or the first portion 105 or the second portion 106 may reflect at least a portion of the light from the light source 102 toward the light sensor 108. The light sensor 108 may measure the amount of light reflected by the joint 112, the first portion 105, or the second portion 106. In one example, the light sensor 108 may be a full spectrum light sensor that may measure light reflected across a full light spectrum. In another example, the light sensor 108 may measure a portion of light reflected within a light spectrum range. In another example, the light sensor 108 may be a still-image camera, a video camera, an infrared sensor, and so forth.

The light sensor 108 may be coupled to a processing device 114. The light sensor 108 may send light measurement information to the processing device 114. The processing device 114 may analyze the light measurement information to determine whether there may be any imperfections or defects in the joint 112, the first portion 105, or the second portion 106 of the object 104. In one example, when the processing device 114 detects an imperfection or a defect in the object 104, the processing device 114 may send an alert notification to a user, such as by displaying an alert on a display or user interface or communicating the notification to another device. In another example, when the processing device 114 does not detect an imperfection or a defect in the object 104, the processing device 114 may send an approval notification to a user, such as by displaying an message on a display or user interface or communicating the notification to another device.

In one example, the processing device 114 may compare the light measurements with a predefined measurement to determine if the amount of light reflected by the object 104 is within an acceptable range that indicates there are not imperfections or defects. When the light measurements are within an acceptable range, the processing device 114 may send the approval notification. When the light measurements are not within the acceptable range, the processing device 114 may send the error notification. In another example, the processing device 114 may compare different portions of the joint 112, the first portion 105, and/or the second portion 106 to determine a contrast level between the different portions. When the contrast level is within an acceptable range, the processing device 114 may send the approval notification. When the contrast level is not within the acceptable range, the processing device 114 may send the error notification.

FIG. 2A shows the object illumination system 100 in FIG. 1 with a light guide 216, according to an embodiment. Some of the features in FIG. 2A are the same or similar to some of the features in FIG. 1 as noted by same reference numbers, unless expressly described otherwise. The light guide 216 may be configured to guide the light emitted from the light elements 110a-c in a desired direction or with a desired radiation pattern. In one example, the light guide 216 may be a diffuser to disperse or spread the light with a defined transmission pattern that is a light diffusion pattern. The light diffusion pattern spreads the light over a surface or surfaces of the object 104. In another example, the light guide 216 may be a focuser that may focus the light with a defined transmission pattern that is a light focusing pattern. The light focusing pattern may focus the light to a single surface of the object 104 multiple surfaces of the object 104 or a portion of the object 104.

In one embodiment, the light guide 216 may be located approximate to an end of the light elements 110a-c that transmit the light. For example, the light guide 216 may include a top surface 218 and a bottom surface 220. The top surface 218 may be relatively flat or smooth and may be beneath the light elements 110a-c to direct the light transmitted from the light elements 110a-c. In one example, there may be a space between the top surface 218 of the light guide 216 and the light transmitting end of the light elements 110a-c. In another example, She top surface 218 of the light guide 216 may abut or be in contact with the light elements 110*a-c*. The bottom surface 220 may be on a distal end of the light guide 216 that is on a side opposite the light elements 110*a-c*. The bottom surface 220 may be a peripheral diffusing portion or a peripheral focusing portion of the light guide 216.

In another embodiment, the light guide 216 may include cavities 222*a-c* to receive at least a portion of the light elements 110*a-c*. For example, the cavity 222*a* may receive at least a portion of the light element 110*a*, the cavity 222*b* may receive at least a portion of the light element 110*b*, and the cavity 222*c* may receive at least a portion of the light element 110*c*. The portion of the light elements 110*a-c* may include a bulb portion of the light elements 110*a-c* or a light transmitting portion of the light elements 110*a-c*. In another example, the cavities 222*a-c* may receive the entire light elements 110*a-c*. The light guide 216 and the light source 102 may be a lighting device to illuminate the object 104.

In one embodiment, the light guide 216 may include one or more materials to provide a threshold light contrast ratio at a desired area at the object 104. For example, the light guide 216 may be a thermoset material, a thermoplastic resin, or a glass material that provides a threshold light contrast ratio at the joint 112 of the object 104. In one example, the light contrast ratio may be an amount of light reflected by the joint 112 versus an amount of light reflected by the first portion 105 or the second portion 106 of the object. In another example, the light contrast ratio may be an amount of light reflected by the first portion 105 versus an amount of light reflected by the second portion 106 of the object. In another example, the light contrast ratio may be an amount of light reflected by a first part of the joint 112 versus an amount of light reflected by a second part of the joint 112. In another example, the light contrast ratio may be an amount of light reflected by a first pan of the first portion 105 versus an amount of light reflected by a second part of the first portion 105. In another example, the light contrast ratio may be an amount of light reflected by a first part of the second portion 106 versus an amount of light reflected by a second part of the second portion 106.

In one embodiment, the threshold for the light contrast ratio may be a threshold light contrast level for the light sensor 108 to distinguish between the different portions or parts of the object 104. In another embodiment, the threshold for the light contrast ratio may be a threshold light contrast level for the light sensor 108 to distinguish between transmissive materials and absorbing materials of the object 104. In another embodiment, the threshold for the light contrast ratio may be a threshold light contrast level for the light sensor 108 to distinguish between the normal material of the object 104 and imperfections or defects of the object 104, as the imperfections or defects may absorb or reflect the light differently than the normal material of the object 104.

In one embodiment, the light source 102 and the light guide 216 may be in contact with the object 104. In another embodiment, the light source 102 and the light guide 216 may be a threshold distance from the object 104. For example, the light source 102 and the light guide 216 may be a defined distance from the object 104 so as to illuminate a desired portion or part of the object 104. In another embodiment, the object 104 may be on a first plane and the light source 102 and the light guide 216 may be coplanar or parallel to the first plane. In another embodiment, the object 104 may be on a first plane and the light source 102 and the light guide 216 may be on a second plane perpendicular to the first plane. In another embodiment, the object 104 may be on a first plane and the light source 102 and the light guide 216 may be on a second plane that is at an angle to the first plane. For example, the second plane may be at an angle to the first plane of 1 degree to 89 degrees. In another example, the second plane may be at a 45-degree angle or a 90-degree angle to the first plane.

The location and angle of the light source 102 and the light guide 216 relative to the object 104 is not intended to be limiting. In one example, the location and angle of the light source 102 and the light guide 216 relative to the object 104 may vary to illuminate different portions or pieces of the object 104. In another example, the location and angle of the light source 102 and the light guide 216 relative to the object 104 may vary to adjust a contrast ratio between the portions or parts of the object 104.

In one embodiment, the light guide 216 may allow a full spectrum of light to pass through the light guide 216 and be guided by the light guide 216. In another embodiment, the light guide 216 may filter one or more wavelengths of light or a range of wavelengths of light to allow one or more wavelengths of light to pass through the light guide 216 and one or more wavelengths of light to be blocked by the light guide 216.

FIG. 2B shows the object illumination system 100 in FIG. 1 with an absorber 224, according to an embodiment. Some of the features in FIG. 2B are the same or similar to some of the features in FIGS. 1 and 2A as noted by same reference numbers, unless expressly described otherwise. In one example, the absorber 224 may be an absorbing compound that is doped or applied to the joint 112, the first portion 105, or the second portion 106 of the object 104. In one example, the absorber 224 may be impregnated or added to the material of the joint 112, the first portion 105, or the second portion 106 of the object 104. In another example, the absorber 224 may be applied to a surface of the joint 112, the first portion 105, or the second portion 106 of the object 104. In another example, the absorber 224 may be applied to part of the joint 112, the first portion 105, or the second portion 106 of the object 104.

In one embodiment, the absorber 224 may be applied to illuminate a part of the object 104. The absorber 224 may increase or decrease a reflection level or absorption level of the part of the object 104 that the absorber 224 is applied to. In one example, the absorber 224 may be applied to the joint 112 to aid in illuminating the joint 112 or provide additional contrast at the joint 112 for the light sensor 108 to measure. In another embodiment, a first part of the first portion 105 may be joined to the second portion 106 using a first joining technique and a second part of the first portion 105 may be joined to the second portion 106 using a second joining technique. The absorber 224 may be applied to the second part to provide additional contrast for the joint 112 formed using the second joining technique. In one example, the first joining technique may be one of a laser welding technique, ultrasonic welding technique, gluing technique, solvent bonding technique, hot plate welding technique, IR welding technique, and so forth and the second joining technique may be another one of the laser welding technique, ultrasonic welding technique, gluing technique, solvent bonding technique, hot plate welding technique, IR welding technique, and so forth .

Figure 2C:
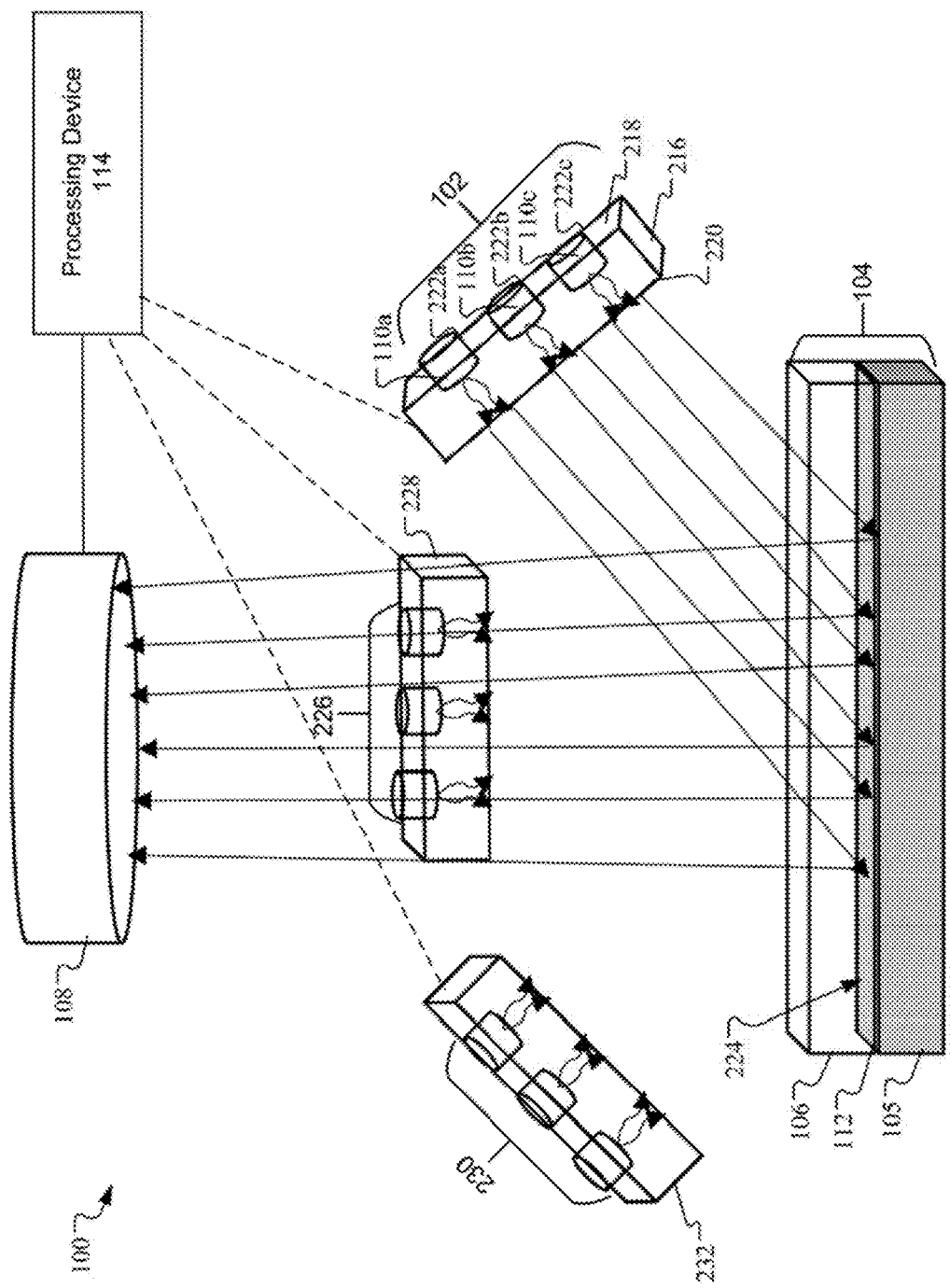
FIG. 2C shows the object illumination system in FIG. 1 with the first light source and the first light guide, a second light source and a second light guide, and a third light source and a third light guide, according to an embodiment.

FIG. 2C shows the object illumination system 100 in FIG. 1 with the first light source 102 and the first light guide 216, a second light source 226 and a second light guide 228, and a third light source 230 and a third light guide 232, according to an embodiment Some of the features in FIG. 2C are the same or similar to some of the features in FIGS. 1 and 2A-2B as noted by same reference numbers, unless expressly described otherwise.

The object illumination system 100 may include multiple light sources and light guides. For example, the object illumination system 100 may include the first light source 102 and the first light guide 216 pair, the second light source 226 and the second light guide 228 pair, and the third light source 230 and the third light guide 232 pair to illuminate the object 104.

In one embodiment, the first light source 102 and the first light guide 216 pair, the second light source 226 and the second light guide 228 pair, and the third light source 230 and the third light guide 232 pair may be located at different positions relative to the object 104. In one example, the first light source 102 and the first light guide 216 pair, the second light source 226 and the second light guide 228 pair, and the third light source 230 and the third light guide 232 pair may each be located at different distances from the object 104. In another example, the first light source 102 and the first light guide 216 pair, the second light source 226 and the second light guide 228 pair, and the third light source 230 and the third light guide 232 pair may each be located at different angles relative to the object 104. In another embodiment, the first light source 102, the second light source 226, and/or the third light source 230 may transmit different wavelengths of light. For example, the first light source 102 may transmit light with a wavelength spectrum between 350 nanometers (nm) to 450 nm, the second light source 226 may transmit light with a wavelength spectrum between 750 nm to 1100 nm, and the third light source 230 may transmit light with a wavelength spectrum between 1700 nm to 2000 nm. The wavelength spectrums are not intended to be limiting. For example, the first light source 102. the second light source 226 or the third light source 230 may transmit light with a wavelength spectrum between 1500 nm and 1600 nm.

In one embodiment, manual switches, firmware, integrated circuits, and so forth may control the tight sources 102, 226, and/or 230. In another embodiment, the processing device 114 may control the light sources 102, 226, and 230. The processing device 114 may turn the light sources 102, 226, and/or 230 on or off to illuminate different parts of the object 104 and/or to increase or decrease an amount of light that illuminates the object 104.

In one example, the processing device 114 may turn the first light source 102 and the second light source 226 on to provide an increased illumination level of the object 104. In another example, the processing device 114 may turn on the first light source 102, the second light source 226, and the third light source 230 at different times or in a sequential order to capture light measurements for light transmitted by the first light source 102, the second light source 226, and the third light source 230, respectively. In another example, when the first light source 102, the second light source 226, and the third light source 230 transmit light at different wavelengths or wavelength spectrums or the first light guide 216, the second light guide 228, or the third light guide 232 filter transmitted light at different wavelengths, the processing device 114 may turn on the different light sources 102, 226, and/or 230 based on the object 104 being illuminated. In one example, when the first portion 105 or the second portion 106 of the object 104 is a first material, the processing device 114 may turn on the first light source 102 to illuminate the object 104 at a first wavelength or wavelength spectrum. In another example, when the first portion 105 or the second portion 106 of the object 104 is a second material, the processing device 114 may turn on the second light source 226 or the third light source 230 to illuminate the object 104 at a second wavelength or wavelength spectrum.

In one embodiment, the processing device 114 may define a baseline measurement using a light measurement from one of the first light source 102, the second light source 226, or the third light source 230. The processing device 114 may then take a second measurement from a different one of the first light source 102, the second light source 226, or the third light source 230 and compare the measurements to determine a variation between the light measurements. When the variation between the measurements exceeds a threshold, the processing device 114 may determine that the object 104 has an imperfection or defect.

When the light sensor 108 captures the various light measurements, the processing device 114 may analyze the light measurements to more accurately identify imperfections or defects. For example, when the first light source 102 illuminates the object 104 at a first distances, angle, or wavelength, the transmitted light may not fully illuminate the imperfections or defects of the object 104, and when the second light source 226 illuminates the object 104 at a second distances, angle, or wavelength, the transmitted light may more fully illuminate the imperfections or defects of the object 104.

FIG. 2D shows the object illumination system 100 in FIG. 1 with the light source 102 and the light guide 216 located below the object 104, according to an embodiment. Some of the features in FIG. 2D are the same or similar to some of the features in FIGS. 1 and 2A-2C as noted by same reference numbers, unless expressly described otherwise. In one embodiment, the light source 102 and light guide 216 may illuminate the object 104 from below the object 104. For example, the object 104 may be located between the light guide 216 and the light sensor 108. In one example, the light elements 110 may be located approximate and below the object 104 and may transmit light through the bottom of the object 104 to the light sensor 108. The light sensor 108 may measure an amount of light absorbed by different parts of the object 104.

Figure 2E:
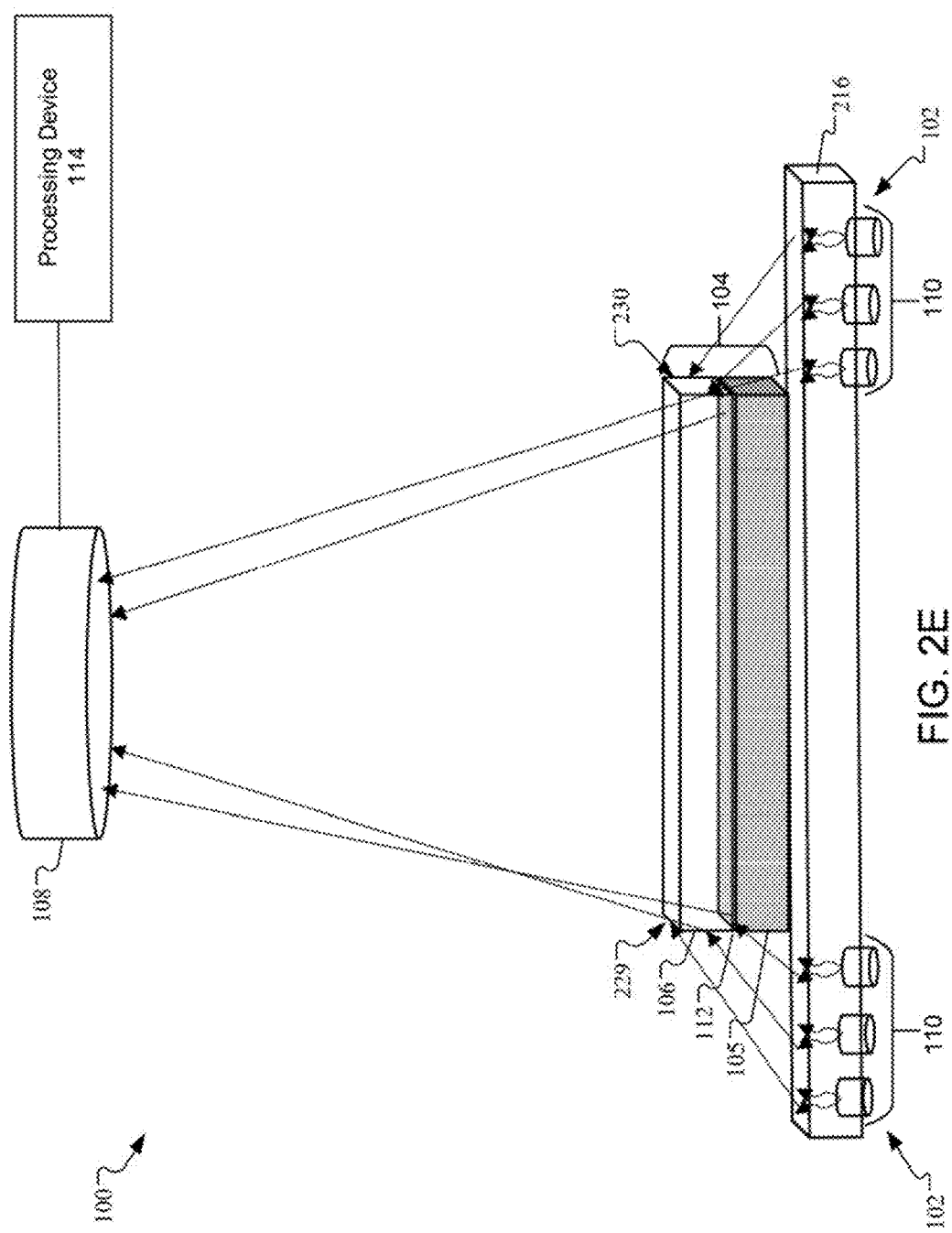
FIG. 2E shows the object illumination system in FIG. 1 with the light guide located below the object and the light elements on the bottom edges of the object, according to an embodiment.

FIG. 2E shows the object illumination system 100 in FIG. 1 with the light guide 216 located below the object 104 and the light elements 110 on the edges of the light guide 216, according to an embodiment. Some of the features in FIG. 2E are the same or similar to some of the features in FIGS. 1 and 2A-D as noted by same reference numbers, unless expressly described otherwise. In one embodiment, the light source 102 and light guide 216 may illuminate the object 104 from the sides 229 and 230 of the object 104. For example, the object 104 may be located between the light guide 216 and the light sensor 108. In one example, the light elements 110 may be located below the object 104, at the side of the light guide 216, and approximate the sides 229 and 230 of the object 104. The light elements 110 may transmit light to the sides 229 and 230 of object 104. The object 104 may reflect at least a portion of the light to the light sensor 108. The light sensor 108 may measure an amount of light reflected by different pans of the object 104.

Figure 2F:
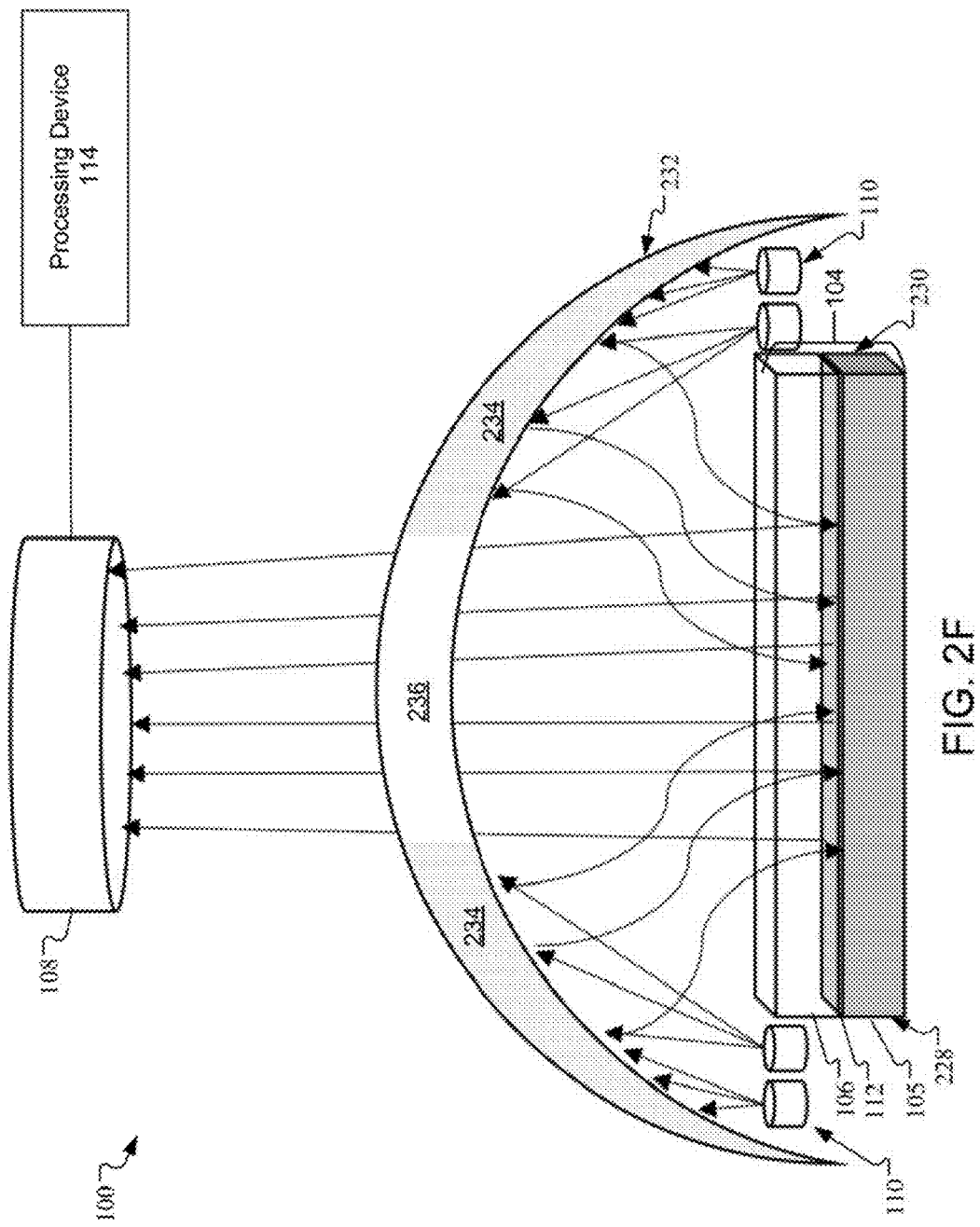
FIG. 2F shows the object illumination system in FIG. 1 with a light guide located above the object and the light elements on the sides edges of the object, according to an embodiment.

FIG. 2F shows the object illumination system 100 in FIG. 1 with a light guide 232 located above the object 104 and the light elements 110 approximate the sides 229 and 230 of the object 104, according to an embodiment. Some of the features in FIG. 2F are the same or similar to some of the features in FIGS. 1 and 2A-E as noted by same reference numbers, unless expressly described otherwise. In one embodiment, the light elements 110 may transmit light approximate the sides of the object 104 toward the light guide 232 located above the object 104. In one example, the light guide 232 may have a conical shape, such as a conical mirror. In another example, the light guide 232 may have a dome shape that fits around a portion of the top of the object 104 and/or the sides 229 and 230 of the object 104. The light guide may include a first portion 234 that may reflect the light from the light elements 110 toward the object 104. The first portion 105, the second portion 106, or the joint 112 of the object 104 may reflect at least a portion of the light toward a second portion 236 of the light guide 232. The first portion 234 of the light guide 232 may reflect the light from the light elements 110 to more fully illuminate at least a pan of the object 104.

The second portion 236 of the light guide 232 may be transmissive or translucent material and allow the light reflected from the object 104 to pass through the second portion 236 of the light guide 232 and reach the light sensor 108. The light sensor 108 may measure the received light and the processing device 114 may analyze the measured light to identify imperfections or defects in the object 104. The location of the light guide 232 is not intended to be limiting. In one example, the light guide 232 may be located below the object 104 or at a side of the object 104.

Figure 3A:
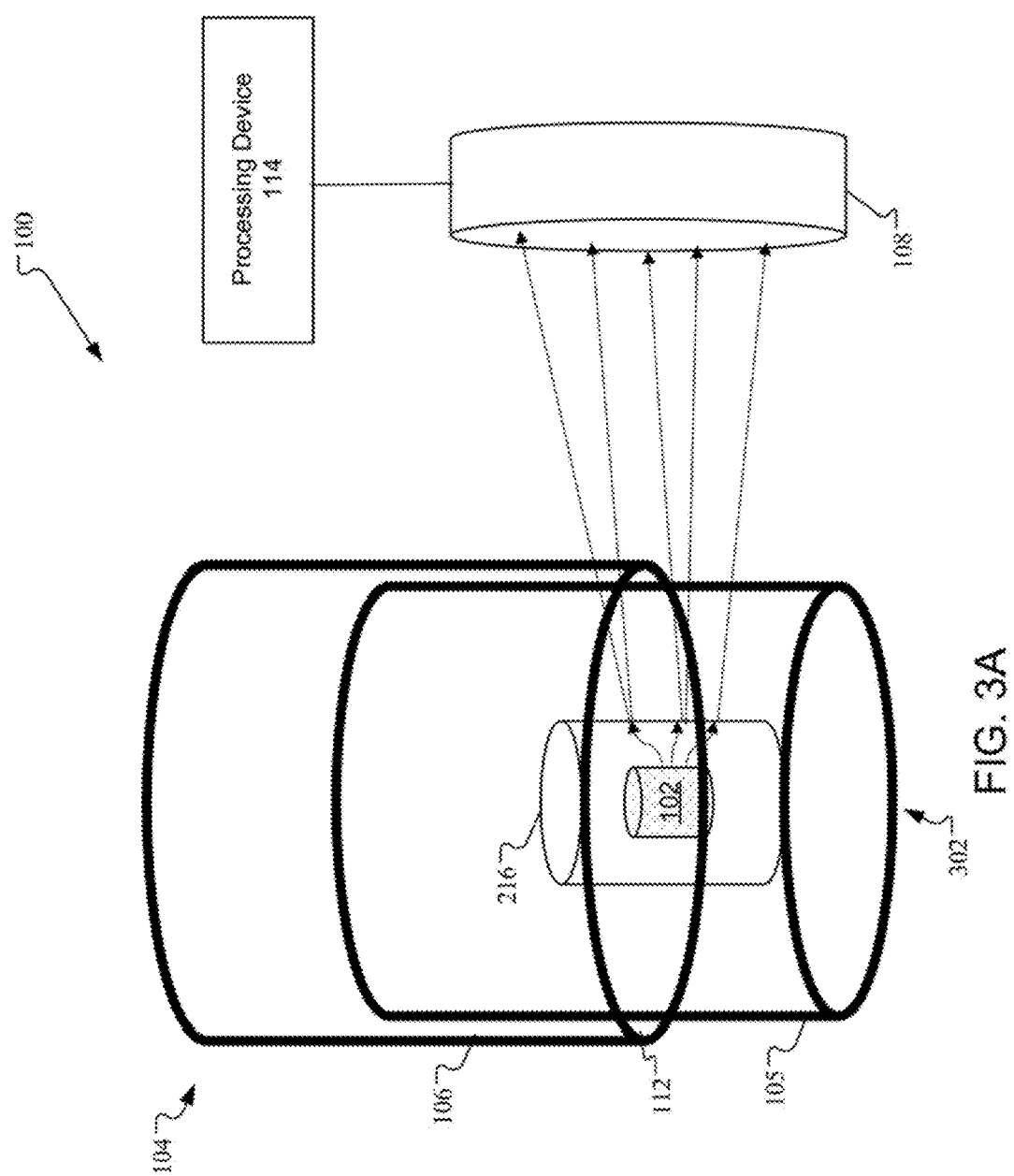
FIG. 3A shows the object illumination system in FIG. 1 with the light source and the light guide located within the object, according to an embodiment.

FIG. 3A shows the object illumination system 100 in FIG. 1 with the light source 102 and the light guide 216 located within the object 104, according to an embodiment. Some of the features in FIG. 3A are the same or similar to some of the features in FIGS. 1 and 2A-F as noted by same reference numbers, unless expressly described otherwise. The object 104 may include a cavity 302. The cavity 302 may be an empty space within the object 104. The light source 102 and the light guide 216 may be shaped to fit within the cavity 302. In one example, the light guide 216 may encapsulate the light source 102. In another example, the light source 102 may fit within a cavity or opening of the light guide 216. In another example, the light source and the light guide 216 may be located approximate the joint 112 or approximate a surface of the object 104.

In one embodiment, when the light source 102 and the light guide 216 are located within the cavity of the object 104, the light guide 216 may diffuse or focus the light from the light source 102 onto a portion of the first portion 105, the second portion 106, and/or the joint 112 of the object 104. In another embodiment, when the light source 102 and the light guide 216 are located within the cavity 302 of the object 104, the light guide 216 may diffuse the light from the light source 102 to substantially illuminate the entire object 104. In one example, the object 104 may be cylinder shaped, square shaped, rectangular shaped, or another shape. The light sensor 108 may measure an amount of light transmitted through the object 104 for analysis by the processing device 114.

Figure 3B:
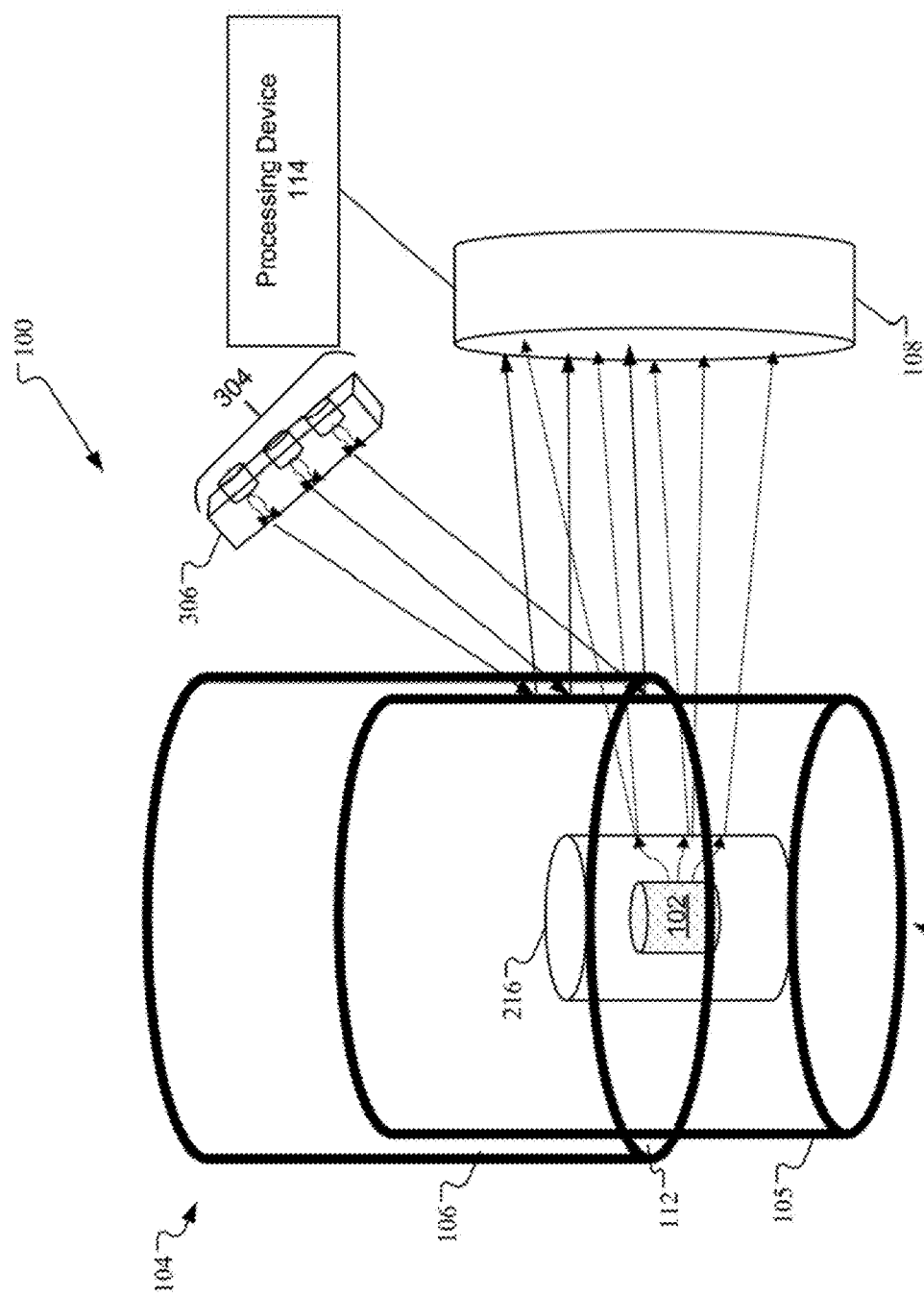
FIG. 3B shows the object illumination system in FIG. 1 with the first light source and the first light guide located within the object and a second light source and a second light guide exterior to the object, according to an embodiment.

FIG. 3B shows the object illumination system 100 in FIG. 1 with the first light source 102 and the first light guide 216 located within the object 104 and a second light source 304 and a second light guide 306 exterior to the object 104, according to an embodiment. Some of the features in FIG. 3B are the same or similar to some of the features in FIGS. 1, 2A-F, and 3A as noted by same reference numbers, unless expressly described otherwise.

The object illumination system 100 may include multiple light sources and light guides located within the object 104 and/or exterior to the object 104. For example, the first light source 102 and the first light guide 216 may be located within the cavity 302 of the object, as discussed above, to illuminate the object 104 from within the cavity 302. The second light source 304 and the second light guide 306 may be located external to the object 104, such as art exterior surface, and transmit light toward the object 104. The light from the second light source 204 may be reflected off the first portion 105, the second portion 106, or the joint 112 of the object 104.

In another embodiment, the first light source 102 and the second light source 304 may transmit different wavelengths of light. For example, the first light source 102 may transmit light with a wavelength spectrum between 350 nanometers (nm) to 450 nm and the second light source 304 may transmit light with a wavelength spectrum between 1500 nm to 1600 nm. The wavelength spectrums are not intended to be limiting. For example, the first light source 102 may transmit at 1550 nm, the wavelength absorbed by water, and the second light source 226 may transmit light at a wavelength between 1700 nm and 2100 nm. In another embodiment, the first light source 102 and the second light source 304 may transmit light at the same or similar wavelength spectrums and the first light guide 216 and the second light guide 306 may filter different wavelengths of light such that light emitted from the first light guide 216 and the second light guide 306 are different wavelengths of light.

Figure 3C:
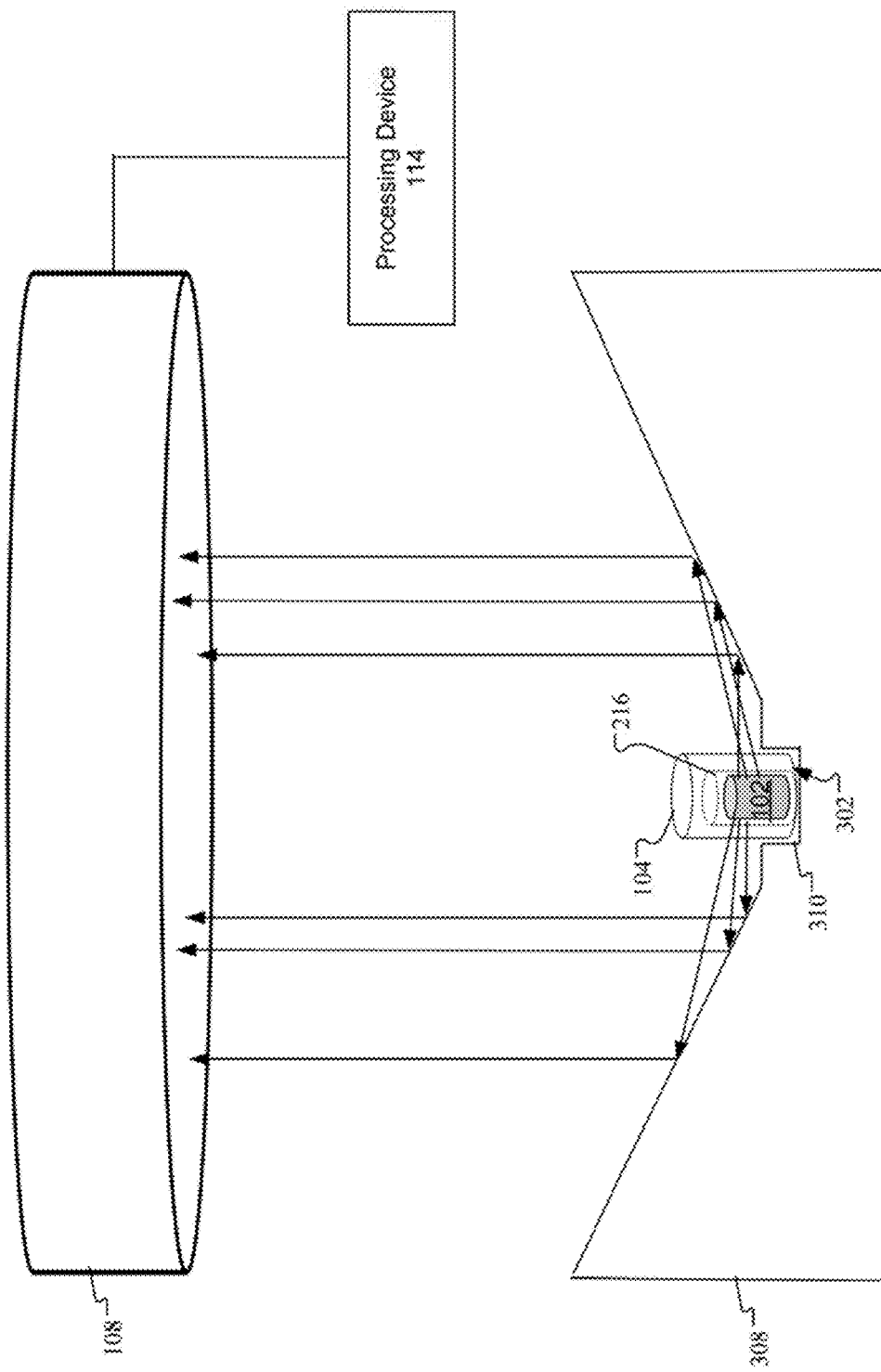
FIG. 3C shows the object illumination system in FIG. 1 with a conical mirror, according to an embodiment.

FIG. 3C shows the object illumination system 100 in FIG. 1 with a conical mirror 308, according to an embodiment. Some of the features in FIG. 30 are the same or similar to some of the features in FIGS. 1, 2A-F, and 3A-3B as noted by same reference numbers, unless expressly described otherwise.

The object illumination system 100 may include the light source 102 and the light guide 216 located within the cavity 302 of the object 104, as in FIG. 3B. In one embodiment, the light source 102, the light guide 216, and the object 104 may be located within a cavity 310 of the conical mirror 308. The cavity 310 may be an indent, groove, or depression in the conical mirror 308. In one example, the cavity 310 may be located at a center of middle of the conical mirror 308. In one example, the conical mirror 308 may be a cone-shaped concave mirror. As light is emitted from the object 104 through the light guide 216 and the object 104, the conical mirror 308 may reflect the light toward the light sensor 108. The conical mirror may reflect the light to increase an amount of light received at the light sensor 108. The increased amount of light received at the light sensor 108 may increase an accuracy of the light measurements used by the processing device 114 to detect imperfections and defects in the object 104.

The disclosure above encompasses multiple distinct embodiments with independent utility. While each of these embodiments has been disclosed in a particular form, the specific embodiments disclosed and illustrated above are not to be considered in a limiting sense as numerous variations are possible. The subject matter of the embodiments includes all novel and non-obvious combinations and sub-combinations of the various elements, features, functions and/or properties disclosed above and inherent to those skilled in the art pertaining to such embodiments. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and sub-combinations of the disclosed embodiments that are believed to be novel and non-obvious. Embodiments embodied in other combinations and sub-combinations of features, functions, elements and/or properties may be claimed through amendment of those claims or presentation of new claims in the present application or in a related application. Such amended or new claims, whether they are directed to the same embodiment or a different embodiment and whether they are different, broader, narrower or equal in scope to the original claims, are to be considered within the subject matter of the embodiments described herein.

The invention claimed is:

1. A system, comprising:
 an object comprising:
  a first portion;
  a second portion; and
  a joint joining the first portion to the second portion;
 a first light source to transmit light toward the object;
 a first light guide approximate to an incident end of the first light source, the first light guide configured to:
  receive at least a portion of the light from the first light source; and
  guide at least the portion of the light within a defined wavelength spectrum toward the object at a first defined transmission pattern; and
 an light sensor to measure at least a portion of the light reflected from the joint of the object.

2. The system of claim 1, wherein the first light guide comprises at least one material to provide a threshold light contrast ratio of material at the joint of the object.

3. The system of claim 2, wherein the at least one material of the first light guide comprises a thermoset material, a thermoplastic resin, or a glass material.

4. The system of claim 1, wherein the first light guide includes a cavity to receive at least a portion of the first light source.

5. The system of claim 1, wherein the first light source and the first light guide are located within a cavity of the object.

6. The system of claim 1, wherein the first light source and the first light guide are located approximate to an exterior surface of the object.

7. The system of claim 1, further comprising:
 a second light source to transmit light toward the object; and
 a second light guide approximate to an incident end of the second light source, the second light guide configured to:
  receive at least a portion of the light from the second light source; and
  guide at least the portion of the light within the defined wavelength spectrum toward the object at a second defined transmission pattern.

8. The system of claim 7, wherein the first light source and first light guide are located within a cavity of the object and the second light source and the second light guide are located approximate to an exterior surface of the object.

9. A light guide:
 a body configured to direct at least a portion of light within a defined wavelength spectrum from a first light source toward an object, the body being formed of a material to provide a threshold contrast ratio between a first portion of the object and a second portion of the object, the body comprising:
  a first surface includes a first cavity formed to receive at least a portion of an incident end the first light source;
  a second surface at a distal end from the light source, the second surface being a peripheral diffusing portion or a peripheral focusing portion.

10. The light guide of claim 9, wherein:
 the first portion of the object is at least one of a translucent material or a absorptive material; and
 the second portion of the object is at least one of translucent material or absorptive material.

11. The light guide of claim 9, wherein the body is to guide at least the portion of the light within a defined wavelength spectrum toward the object at a defined transmission pattern.

12. The light guide of claim 11, wherein the defined transmission pattern is a light diffusion pattern or a light focusing pattern.

13. The light guide of claim 9, wherein the light guide is located within a cavity of the object, located approximate a joint between the first portion of the object and the second portion of the object, or located approximate a surface of the object.

14. The light guide of claim 9, wherein the first surface includes a second cavity formed to receive at least a portion of an incident end of a second light source.

15. The light guide of claim 9, wherein the body comprises at least one of a thermoset material, a thermoplastic resin, or a glass material.

16. The light guide of claim 9, wherein the wavelength spectrum is at least one of 350 nanometers (nm) to 450 nm, 750 nm to 1100 nm, 1500 nm to 1600 nm, or 1700 nm to 2000 nm.

17. A lighting device:
 a light source to transmit light toward an object;
 a light guide approximate to an incident end of the light source configured to:
  receive at least a portion of the light from the light source;
  guide at least the portion of the light within a defined wavelength spectrum toward the object at a defined transmission pattern; and
  provide a threshold contrast ratio between a first portion of the object and a second portion of the object.

18. The lighting device of claim 17, wherein the light guide comprises a material to provide the threshold contrast ratio for the defined wavelength spectrum of light at a joint of the object.

19. The lighting device of claim 17, wherein the light guide is located within a cavity of the object.

20. The lighting device of claim 17, further comprising a conical mirror to reflect at least a portion of the light reflected by the object.

* * * * *